United States Patent
Kolmogorov et al.

(10) Patent No.: US 7,123,757 B2
(45) Date of Patent: Oct. 17, 2006

(54) MOTION ORGANIZED SIMULTANEOUS ACQUISITION WITH INTERACTIVE CONTROL FOR FAST REAL-TIME NAVIGATOR GUIDED IMAGING

(75) Inventors: Vladimir N. Kolmogorov, New York, NY (US); Yi Wang, Pittsburgh, PA (US); Ramin Zabih, New York, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 859 days.

(21) Appl. No.: 10/164,502

(22) Filed: Jun. 6, 2002

(65) Prior Publication Data

US 2002/0188191 A1    Dec. 12, 2002

Related U.S. Application Data

(60) Provisional application No. 60/296,840, filed on Jun. 8, 2001.

(51) Int. Cl.
*G06K 9/00* (2006.01)
(52) U.S. Cl. ..................................... 382/128
(58) Field of Classification Search ................ 382/128, 382/131, 107, 168
See application file for complete search history.

(56) References Cited

U.S. PATENT DOCUMENTS 5,122,747 A    6/1992    Riederer et al.
5,947,900 A *  9/1999    Derbyshire et al. ......... 600/410

(Continued)

OTHER PUBLICATIONS

R.S. Hinks, Monitored Echo Gating (MEGA) for the Reduction of Motion Artifacts, 1 page, Sixth Annual Meeting Program and Abstracts, SMIR, p. 48, 1988.
T.S. Sachs et al.; The Diminishing Variance Algorithm for Real-Time Reduction of Motion Artifacts in MRI; 11 pages; Magn Reson Med. 1995; 34(3):412-22.
Y. Wang et al., Navigator-Echo-based Real-Time Respiratory Gating and Triggering for Reduction of Respiration Effects in Three-dimensional Coronary MR Angiography; 6 pages; Radiology, 1996; 198(1):55-60.
P. Jhooti et al., Phase Ordering With Automatic Window Selection (PAWS): A Novel Motion-Resistant Technique for 3D Coronary Imaging; 11 pages; Magn Reson Med 43:470-480 2000.
T.S. Sachs et al, Real-Time Motion Detection in Spiral MRI Using Navigators, 7 pages, Magn Reson Med., 32(5):639-45 1994.

(Continued)

*Primary Examiner*—Jingge Wu
*Assistant Examiner*—Tom Y. Lu
(74) *Attorney, Agent, or Firm*—Reinhart Boerner Van Deuren P.C.

(57) ABSTRACT

An efficient navigator method is presented that substantially increases the scan efficiency while maintaining the motion suppression effectiveness in magnetic resonance imaging. The method is achieved by simultaneously acquiring different image volumes at different motion states of the subject being scanned. A scheduling algorithm is used to assign volumes to position bins of a motion histogram of the subject. The motion histogram is periodically updated and the volumes are reassigned to position bins.

29 Claims, 9 Drawing Sheets

U.S. PATENT DOCUMENTS

| | | |
|---|---|---|
| 6,073,041 A | 6/2000 | Hu et al. |
| 6,472,872 B1 | 10/2002 | Jack, Jr. et al. |
| 6,516,210 B1 | 2/2003 | Foxall |
| 6,556,009 B1 | 4/2003 | Kellman et al. |
| 6,617,850 B1 | 9/2003 | Welch et al. |
| 6,791,323 B1 * | 9/2004 | Wang et al. ................ 324/309 |
| 6,947,585 B1 * | 9/2005 | Jones ......................... 382/131 |
| 7,003,343 B1 * | 2/2006 | Watts et al. ................ 600/410 |

OTHER PUBLICATIONS

Y. Wang et al.; 3D MR Angiography of Pulmonary Arteries Using Real-time Navigator Gating and Magnetization Preparation; 9 pages; Magn Reson Med. 36(4):579-87 1996.

* cited by examiner

MOTION ORGANIZED SIMULTANEOUS ACQUISITION WITH INTERACTIVE CONTROL FOR FAST REAL-TIME NAVIGATOR GUIDED IMAGING

FIELD OF THE INVENTION

The present invention relates generally to medical diagnosis, and more particularly relates to MRI data acquisition.

BACKGROUND OF THE INVENTION

Magnetic resonance imaging (MRI) is the method of choice for noninvasive diagnosis of soft tissue disease in humans, and has wide applications in cardiovascular diseases. Fast gradient technology has made high-resolution 3D imaging possible, including magnetic resonance angiography (MRA) of coronary and pulmonary arteries. However, the acquisition time for high quality, high resolution data is on the order of minutes. Artifacts from physiological motion occurring during data acquisition, such as respiration and cardiac contraction, degrade image quality and result in blurring or ghosting.

Figure 9:
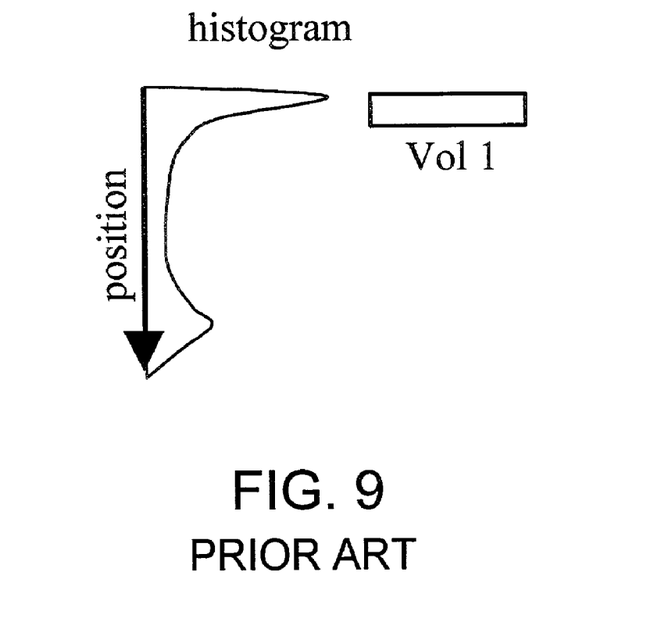
FIG. 9 is a graphical representation of a single volume for scanning near the peak of the subject's motion histogram.

Industry responded by developing methods to suppress the artifacts caused by physiological motion. One suppression approach is the real-time navigator method, which monitors respiration and controls data acquisition accordingly in real-time. Most current navigator techniques are based on gating and they reconstruct images only using data acquired when motion is in a specified window. In these navigator techniques, a motion tolerance window (e.g., gating window) is specified and only the data that is within the specified window is used to construct images. Effective motion suppression requires a small gating window that leads to a long scan time, resulting in inefficiencies. Typically, a single image volume at a window near the most likely motion position, as indicated by the peak of the subject's motion histogram, is taken as represented in FIG. 9. Currently, one of the most efficient methods available is the phase ordering with automatic window selection method (i.e. PAWS), which is optimized against variation in the subject's respiration pattern. In the PAWS method, a fraction of the total scan time corresponding to a small gating window is used for image acquisition. Data at other motion levels are not useable. As a result, scan time is wasted when the subject's position is outside the gating window.

BRIEF SUMMARY OF THE INVENTION

In view of the foregoing, it is a general aim of the present invention to enhance the efficiency of data acquisition in MRI systems.

In that regard, it is an object to acquire different image volumes at different motion positions simultaneously using multiple gating windows while preserving the effectiveness of motion effects suppression.

A feature of the present invention is to utilize algorithms which employ scheduling algorithms based on motion histograms to assign volumes to position bins for scanning.

A further feature is to dynamically update motion histograms and assign volumes to position bins while preserving the effectiveness of motion effects suppression.

Other objectives and advantages of the invention will become more apparent from the following detailed description when taken in conjunction with the accompanying drawings.

BRIEF DESCRIPTION OF THE DRAWINGS

The accompanying drawings incorporated in and forming a part of the specification illustrate several aspects of the present invention, and together with the description serve to explain the principles of the invention. In the drawings.

While the invention will be described in connection with certain preferred embodiments, there is no intent to limit it to those embodiments. On the contrary, the intent is to cover all alternatives, modifications and equivalents as included within the spirit and scope of the invention as defined by the appended claims.

DETAILED DESCRIPTION OF THE INVENTION

Turning to the drawings, wherein like reference numerals refer to like elements, the invention is illustrated as being implemented in a suitable MRI data acquisition environment. Although not required, the invention will be described in the general context of computer-executable instructions, such as program modules, being executed by a personal computer. The invention may also be practiced in distributed computing environments where tasks are performed by remote processing devices that are linked through a communications network.

Figure 1:
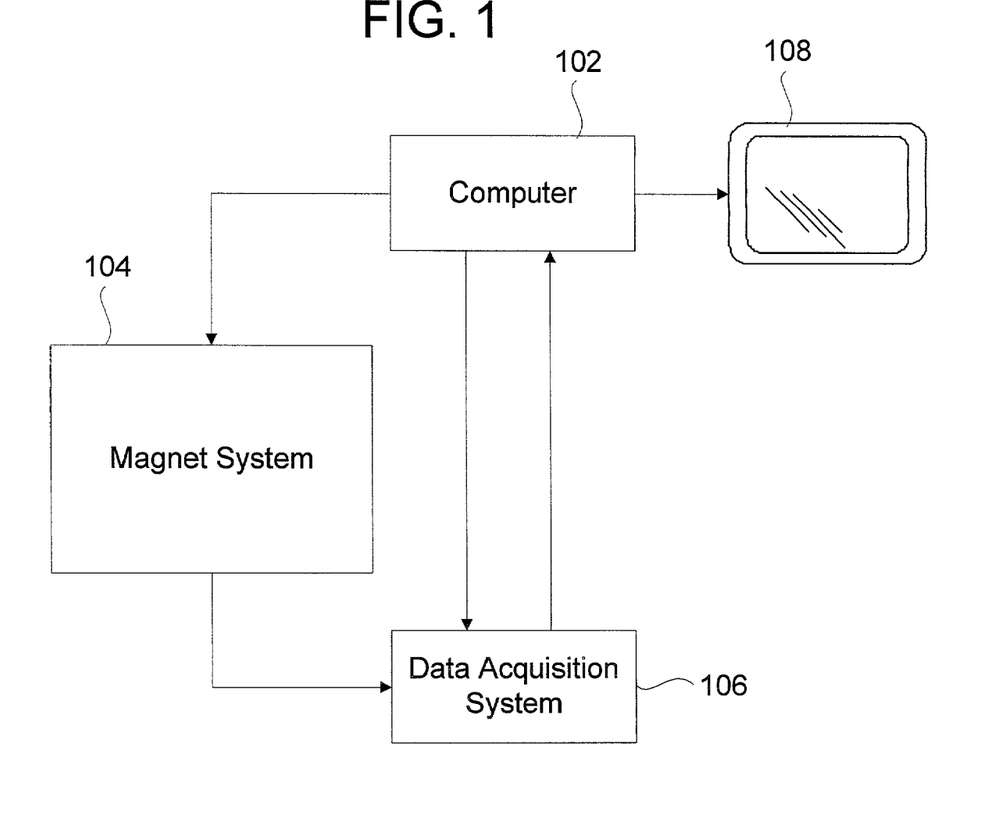
FIG. 1 is a block diagram generally illustrating an exemplary computer system on which the present invention resides.

With reference to FIG. 1, a block diagram of an exemplary system 100 for implementing the invention is shown. The exemplary system includes a computer 102, a magnet system 104, a data acquisition system 106, and display 108. In general terms, the computer 102 controls the gradient and RF magnets or coils (not shown) in the magnet system 104 via amplifiers (not shown). The computer 102 also controls the data acquisition system 106, processes the data acquired, and outputs an image to display 108. Computer 102 typically includes a variety of computer readable media. Computer readable media can be any available media that can be accessed by computer 102 and includes both volatile and nonvolatile media, removable and non-removable media.

Figure 2:
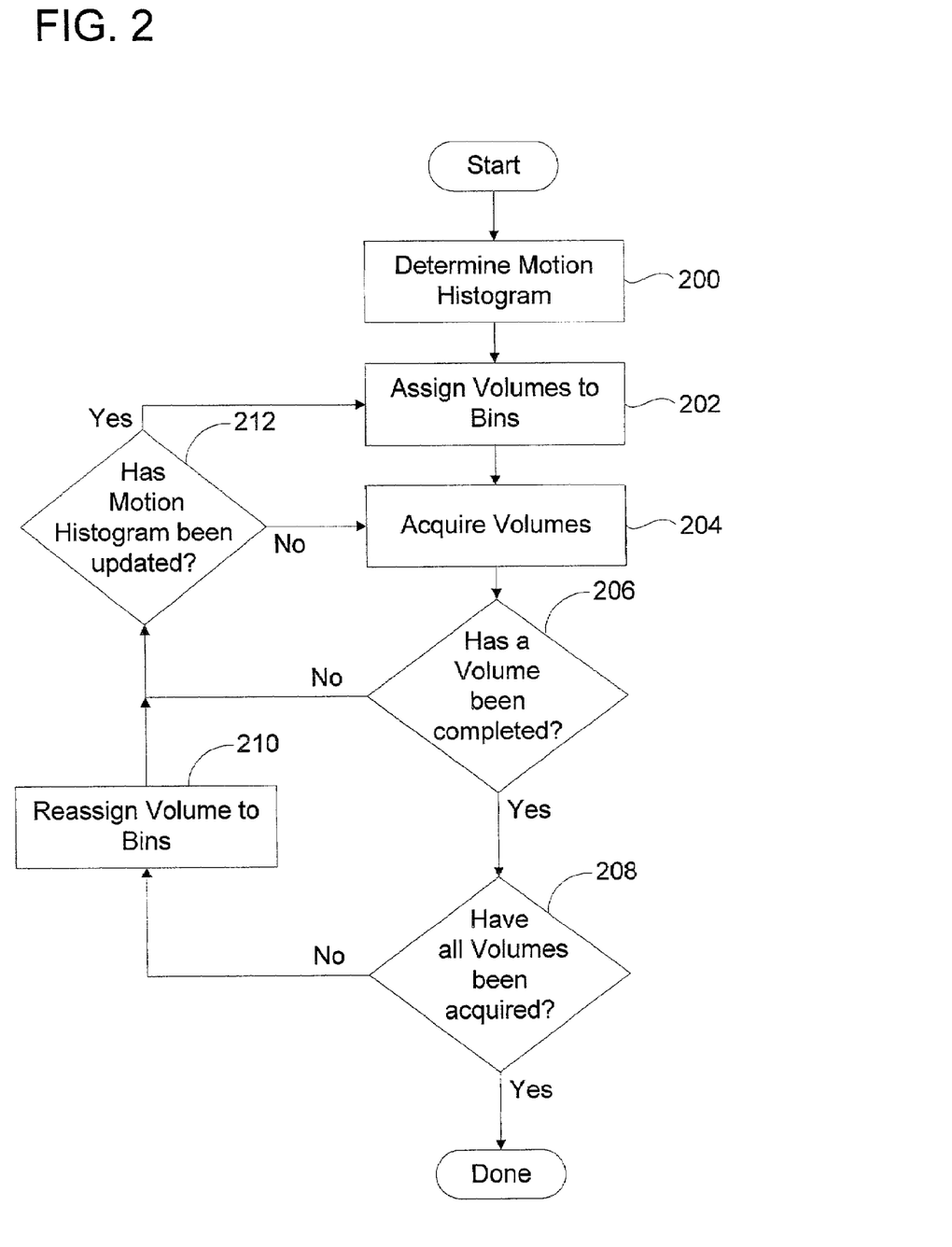
FIG. 2 is a flow chart of a process for acquiring different image volumes at different motion positions simultaneously in accordance with the present invention.
Figure 3A:
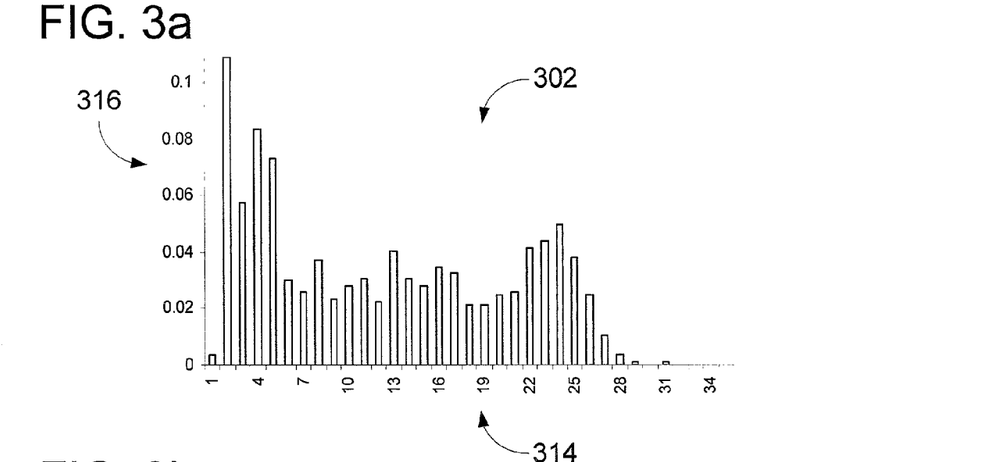
FIGS. 3a–3f are examples of respiratory histograms for different subjects.
Figure 3B:
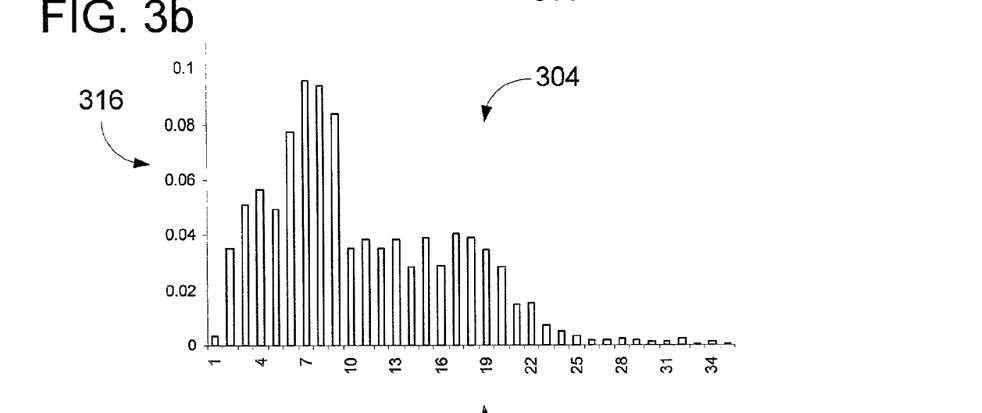
Figure 3C:
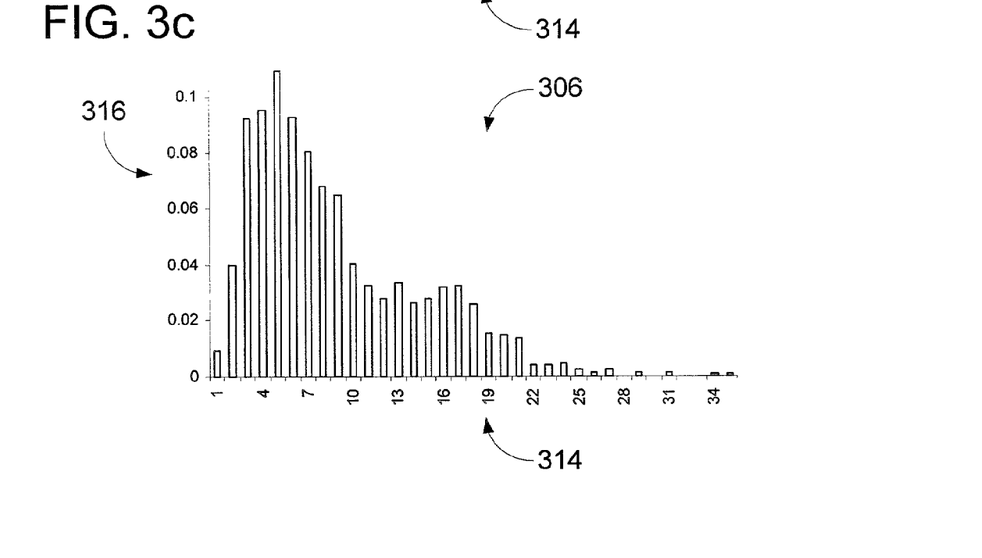
Figure 3D:
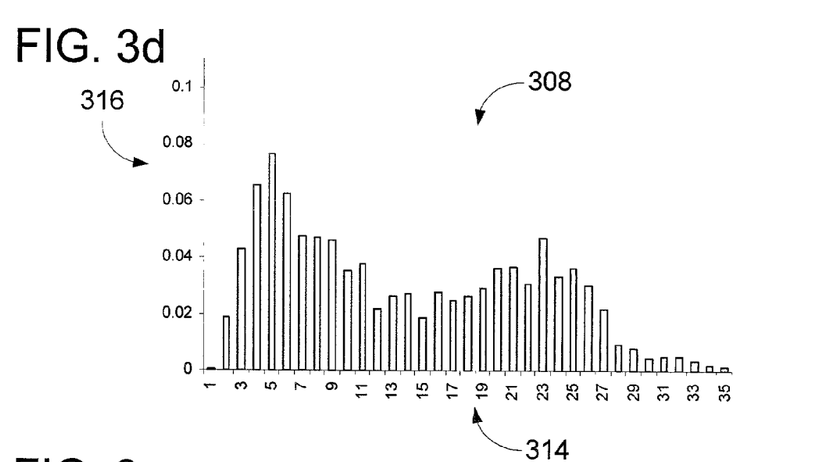
Figure 3E:
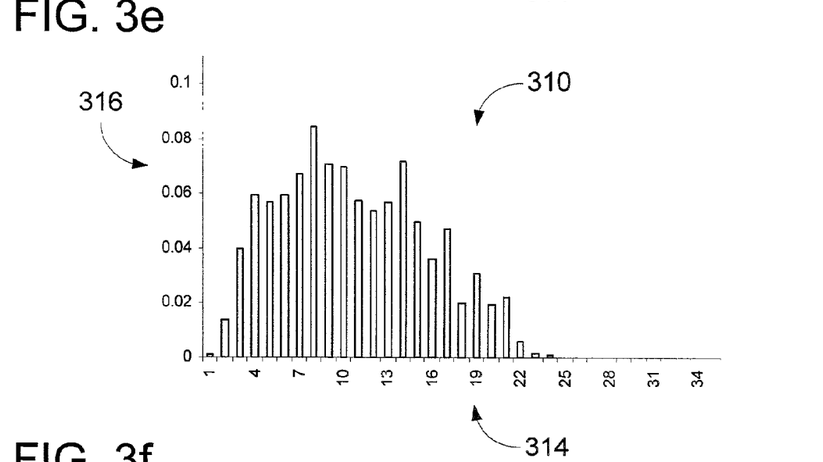
Figure 3F:
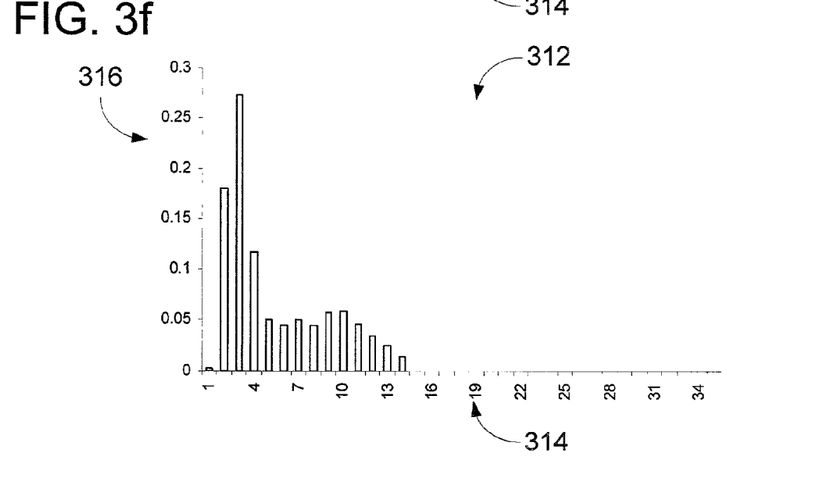

FIG. 2 shows a flow diagram of the steps taken to simultaneously acquire volumes. Those skilled in the art will recognize that some of the steps shown being performed sequentially can be performed in parallel. The steps taken involve first determining the motion histogram of the subject (e.g., patient) (step 200). The respiration varies with time and with each subject. This can be seen in FIGS. 3a–3f, which show respiratory histograms 302–312 of six subjects acquired during a data acquisition. The respiratory histograms 302–312 (i.e., motion histograms) show the probability 316 that the subject will be at a position 314. The motion histogram can be estimated by applying a scan to sample data in an initialization phase and estimating the subject's behavior based on the sampled data. The estimated motion histogram may be fitted with a Gaussian distribution to identify locations for data acquisitions and is divided into position bins. Each position bin corresponds to a position 314 and a probability 316. For example, bin 2 of histogram 302 corresponds to a position that has a probability of greater than 0.1.

Figure 4A:
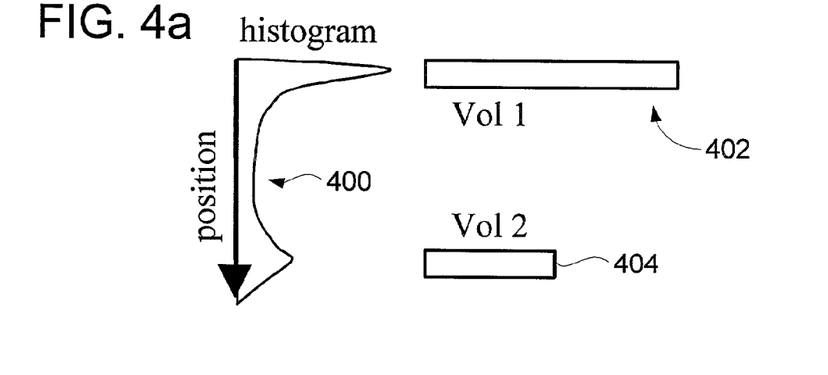
FIGS. 4a–4d are graphical representations of assigning volumes for scanning to motion position.
Figure 4B:
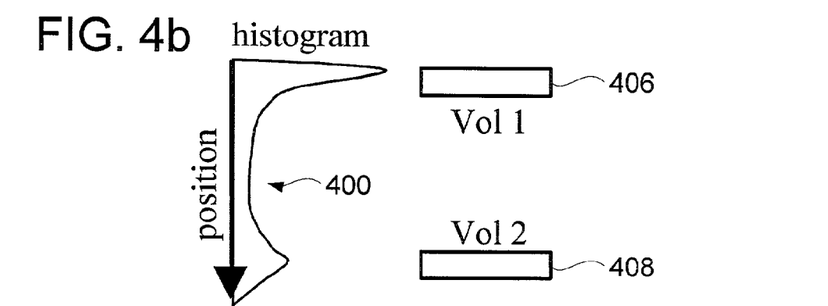
Figure 4C:
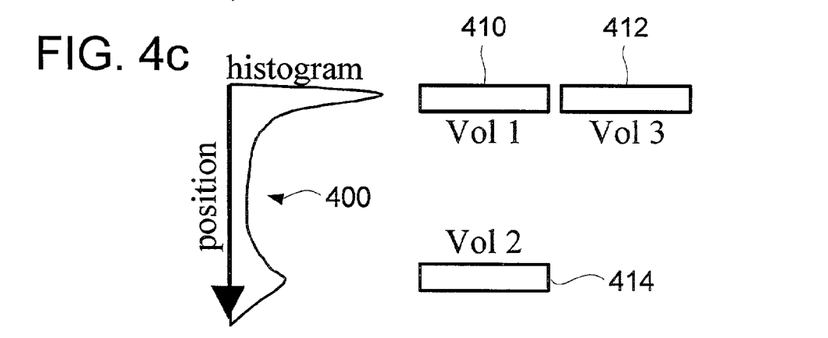
Figure 4D:
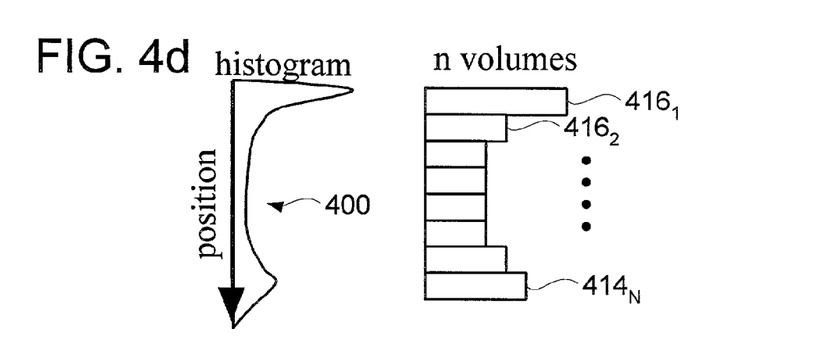

Once the motion histogram is determined, the image volumes to be acquired are assigned to position bins (step 202). The size of each volume is typically selected to be proportional to the height of the histogram peak at that position. Alternatively, the volumes can be equal in size with multiple volumes assigned to a position bin or different in size with multiple volumes assigned to a position bin. FIGS. 4a to 4d illustrate assigning volumes to position bins where the motion histogram 400 has two peaks of different heights. FIG. 4a shows two volumes 402, 404 having sizes proportional to their corresponding histogram peak heights assigned to position bins. FIG. 4b shows two volumes 406, 408 of equal size assigned to two position bins having different histogram peak heights. FIG. 4c shows three volumes 410–414 of equal size assigned to two position bins having different histogram peak heights. FIG. 4d shown n volumes $416_1$ to $416_n$ of different or equal sizes assigned to n position bins.

The image volumes are then acquired (step 204) until one of the image volume data acquisitions is completed (step 206). If all image volumes have been acquired, the process finishes. If all image volumes have not been acquired when one of the image volume data acquisitions is completed (step 208), some or all of the remaining image volumes to be acquired are reassigned to position bins (step 210) and the data acquisition of image volumes continues. In one embodiment, the motion histogram is updated periodically during data acquisition (step 216). When this happens, some or all of the image volumes being acquired are reassigned to position bins and the process continues.

In one embodiment, a scheduling algorithm determines which volumes are assigned to each of the position bins. When the histogram varies in time, the instantaneous histogram, estimated periodically from several immediate past cycles, is updated periodically during data acquisition, and the assignment of volumes to position bins is updated according to the instantaneous histogram using the scheduling algorithm. In general, a scheduling algorithm can be described as follows. There are m parallel processors and n independent jobs. Each job is assigned to one of the processors and has to be completed by the same processor. The processing of job j on the processor i requires time T(ij). The scheduling algorithm determines a schedule that minimizes the completion time of all jobs.

In the present invention, the parallel processors are the position bins and the jobs are the selected volumes. The direct parallel problem is to assign each volume to some position bin such that the scan time is minimal subject to the constraint that upon completion each volume is acquired at a single bin. Let N(v) be the total number of data points in a volume v, $h_b$ the frequency of the instantaneous histogram at bin b, n(v,b) the number of points acquired for volume v at bin b. The time to complete volume v at bin b is $$T(v,b)=(N)(v)-n(v,b))/h_b$$

The scheduling algorithm may leave some bins unassigned. These bins are assigned heuristically to some volumes, which may be useful when histogram changes. Since the histogram hb can change in certain patients, the histogram is updated periodically, and the scheduling algorithm is rerun with updated T(v,b) to adapt the volume acquisition to these changes. This allows any data that was acquired at these position bins to be used in the event that images are acquired at these position bins due to the change in the motion histogram. In one embodiment, the histogram and scheduling is updated every 25 navigator echoes. An exact optimal schedule can be determined using the procedure of depth first search with backtracking and pruning.

An example of the process of the present invention to complete 6 volumes designated as a–f is illustrated in FIGS. 5a–5e. In these figures, the motion histogram 500 is divided into position bins 502–512. The letters a–f indicate different volumes being acquired and the number of letters indicate the amount of data acquired in the correspondingly labeled volumes relative to each other. The motion histogram 500 is scaled such that the frequency of the fastest bin (bin 504) is 1. A scheduling algorithm determines which volumes are assigned initially to each of the position bins 502–512. For purposes of illustration, the assignment is decided at the beginning of data acquisition based on the motion histogram 500: acquire volumes a and f at position bin 504, volumes b and e at position bin 512, volume c at position bin 506, and volume d at position bin 502. Those skilled in the art will recognize that a variety of scheduling algorithms may be used.

Figure 5A:
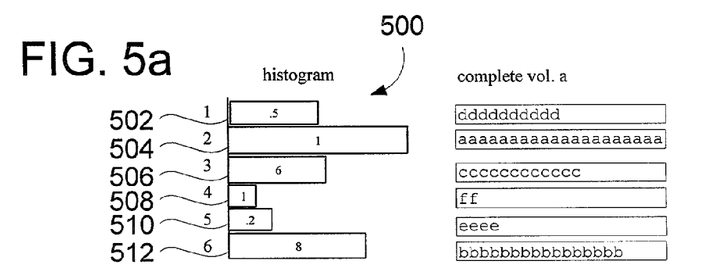
FIGS. 5a–5e illustrate an example of acquiring 6 volumes simultaneously in accordance with the teachings of the present invention.
Figure 5B:
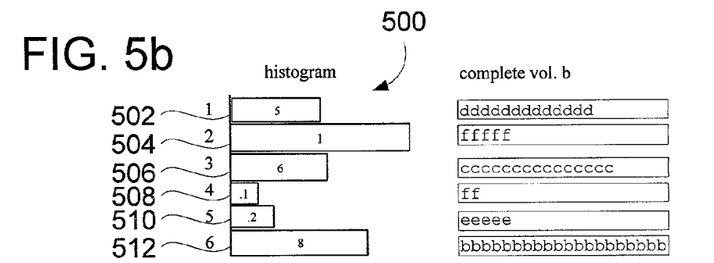
Figure 5C:
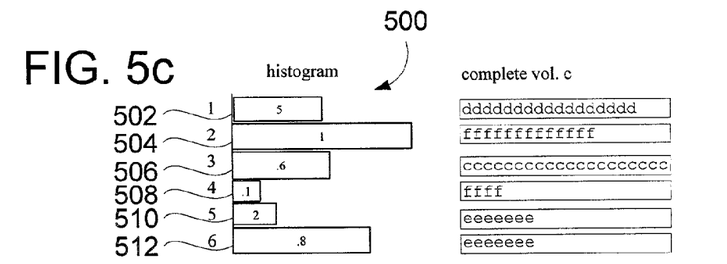
Figure 5D:
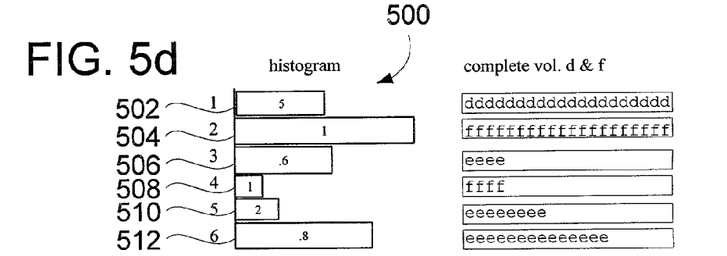
Figure 5E:
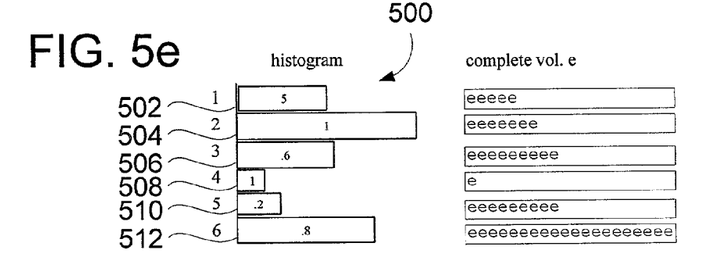

In this example, position bins 508 and 510 are not really used, but it is useful to assign volumes to them in case the motion histogram changes in the future and the probability of position bins 508 and 510 increases. This allows any data that was acquired at these position bins to be used in the event the position bins are associated with a higher probability due to the change in the motion histogram and the image acquisition occurs in one of the position bins. In this example, volume a is acquired and completed using the fastest motion position bin 504 while acquiring volume b at position bin 512, volume c at position bin 506, volume d at position bin 502, volume e at position bin 510, & volume f at position bin 508. After acquisition of volume a is completed as illustrated in FIG. 5a, volume f is reassigned to the fastest position bin 504 and reacquired (because position bin 508 is too slow), while acquisitions are continuing at other position bins until volume b acquisition is completed at bin 512 (see FIG. 5b). Volume f remains at position 508 in case the motion histogram changes and position bin 508 has a higher probability. This allows the acquisition to be completed faster in the motion histogram changes since data has already been acquired at that position. After acquisition of volume b is completed at position bin 512, volume e is reassigned to position bin 512 and data is reacquired (because bin 510 is slow). Volume e remains at position 510 in case the motion histogram changes and position bin 510 has a higher probability. Acquisition of the remaining volumes continues until acquisition of volume c at position bin 506 is completed (see FIG. 5c). Volume e is then also assigned to position bin 506 and reacquired so that if the motion histogram changes, volume e has a higher probability of being completed faster since it is already being acquired at three of the position bins. Volume d at position bin 502 and volume f at position bin 504 are then acquired (see FIG. 5d). Volume e is then assigned to positions 502 and 504 while being acquired at the other position bins. Volume e acquisition then completes at bin 512. In this example, if the time to complete one volume at bin 504 is one unit, then the total scan time is 2.5 units, which results in the present invention reducing the total acquisition scan time by a factor of 2.4 when compared to the acquisition time using only the fastest bin. In the above example, the motion histogram did not change during the acquisitions. Those skilled in the art will recognize that scheduling the acquisition (i.e., assigning volumes to bins and acquiring the volumes) in the case of a varying histogram can be done in a manner similar to FIGS. 5a–5f.

Experiments were performed on 6 healthy subjects to image the right lung, the heart and the left lung simultaneously on a 1.5 T scanner equipped with real-time scan modification capability (CVi Signa, General Electrical Medical System, Milwaukee). The pulse sequence was an ECG-triggered fat-suppressed segmented 3D fast gradient echo sequence. One 2D pencil beam navigator echo positioned at the anterior right diaphragm dome was acquired immediately before the fat suppression pulse at the beginning of data acquisition in each heartbeat to monitor respiration at the diaphragm. The diaphragm position was detected in less than 1 msec using an algorithm consisting of 1) first locating the maximal spatial derivative of the navigator intensity profile for a quick rough estimate of the edge position of the diagram and 2) then improving the accuracy of estimation by searching around the first estimate using the least squares algorithm. The imaging parameters for the 3D acquisition were 30 cm FOV (field of view), 256×160×32 matrix, 0.8 phase FOV, 16 kHz receiver bandwidth, TR/TE=4.5/1.1, body coil for RF transmission, and 4-element phased array coil (cardiac coil) for RF reception.

Figure 6A:
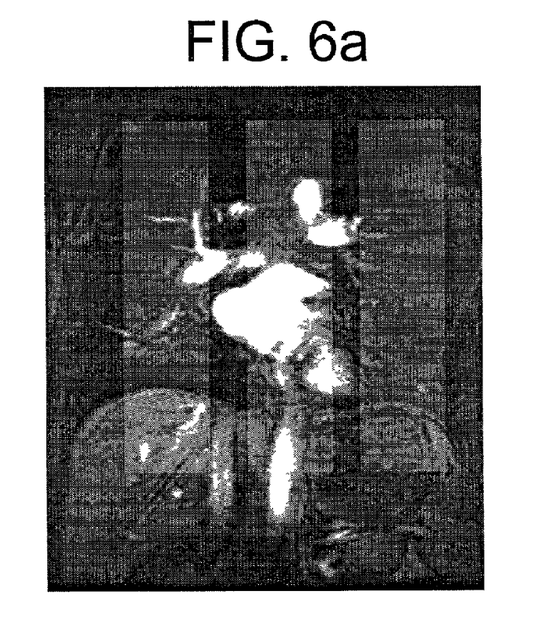
FIG. 6a is a photo showing 3 sagittal volumes highlighted for imaging the right lung, heart, and left lung.
Figure 6B:
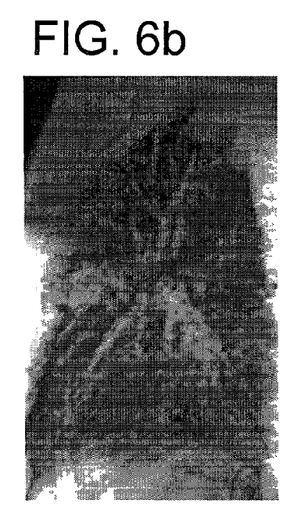
FIG. 6b is a photo of an acquisition of a right lung acquired without the method of the present invention.
Figure 6C:
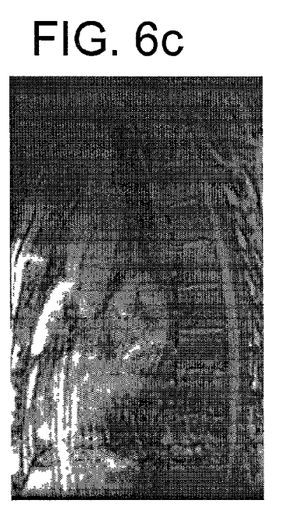
FIG. 6c is a photo of an acquisition of a heart acquired without the method of the present invention.
Figure 6D:
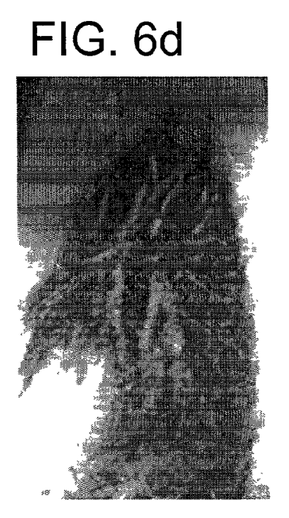
FIG. 6d is a photo of an acquisition of a left lung acquired without the method of the present invention.
Figure 6E:
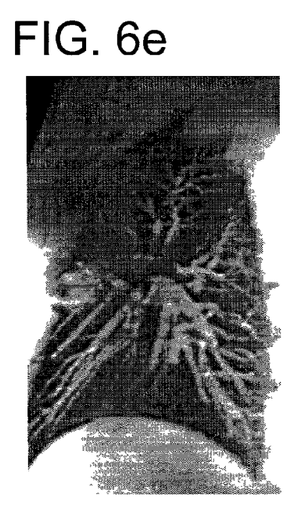
FIG. 6e is a photo of an acquisition of the right lung of FIG. 6b acquired with the method of the present invention.
Figure 6F:
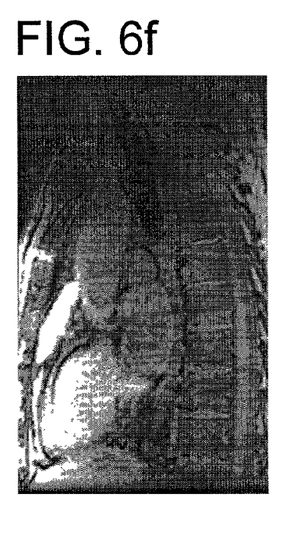
FIG. 6f is a photo of an acquisition of the heart of FIG. 6c acquired with the method of the present invention.
Figure 6G:
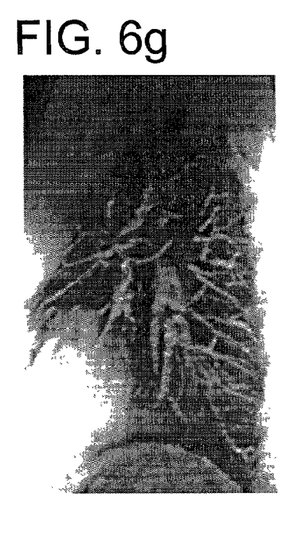
FIG. 6g is a photo of an acquisition of the left lung of FIG. 6d acquired with the method of the present invention.

FIGS. 6a–6g show the images acquired from scanning three image volumes using the steps outlined in FIG. 2. Two volumes were acquired at the larger of the two peaks of a typical motion histogram and one volume was acquired at the smaller of the two peaks. In FIG. 6a the locations of the three sagittal volumes (i.e., image volumes) being acquired are highlighted. FIGS. 6b–6d show images acquired without using the methods of the present invention and FIGS. 6e–6g show images acquired when the methods of the present invention are used. FIGS. 6b and 6e show the images acquired for the right lung, FIGS. 6c and 6f show the images acquired for a section of the heart, and FIGS. 6d and 6g show the images acquired for the left lung.

It can be seen that the images acquired with the present invention are clearer. Results from the 3-volume experiment (i.e., scanning three image volumes simultaneously) using the present invention show that the increase in navigator efficiency of the present invention ranged from 0 to 50% (average 22.5%) over the PAWS method. In one of the subjects tested, the scan time for the 3-volume experiment was 1058 heartbeats. Within the same duration of heartbeats, only 2.06 volumes could be completed by the PAWS method. This corresponds to a navigator efficiency increase of 45.6% while image quality remained the same. The efficiency for the PAWS method was computed as follows: the sequential acquisitions of the same three volumes were simulated using PAWS running on the same navigator waveform. This increase in navigator efficiency is significant using a one-tail paired two-sample t-test (p=0.02). It should be noted that the average increase in efficiency for a 2-volume case is less than that for the 3-volume case. Using the present invention, navigator efficiency can approach 100% with a stable motion histogram and with the volume sizes varied according to the histogram heights such that the acquisitions for all volumes are completed in parallel as taught by the present invention.

Figure 7A:
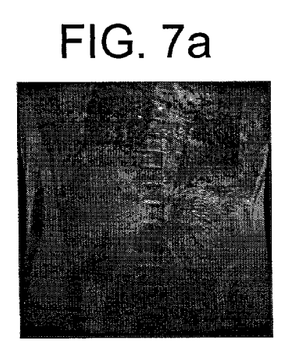
FIG. 7a is a photo of an acquisition of an image acquired with free-breathing.
Figure 7B:
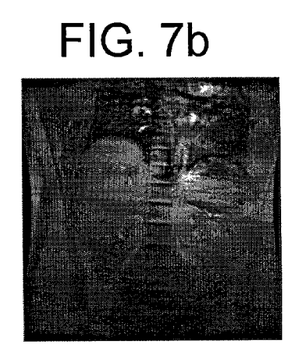
FIG. 7b is a photo of an acquisition of the image of FIG. 7a acquired with the method of the present invention.
Figure 7C:
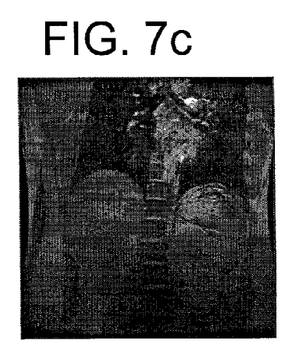
FIG. 7c is a photo of an acquisition of the image of FIG. 7a acquired with breath-holding.

In subsequent tests, the simultaneous acquisition method of the present invention was implemented with a a 2D gradient echo sequence to acquire multiple sections in 7 humans. The real-time data/command communication was done on a SUN workstation connected to a 1.5 T GE CVi scanner via BIT3 cable and socket protocol. The navigator was acquired from the diaphragm using a 2D excitation. The simultaneous acquisition method was compared to acquisitions under free breathing and breath-hold. FIG. 7a is a representative image acquired under free-breathing. FIG. 7b is a representative image acquired using the method of the present invention and FIG. 7c is a representative image acquired using breath-holding. It can be seen that the simultaneous acquisition method of the present invention is consistently better than that under free breathing and provided similar image quality as that under breath-hold.

Figure 8:
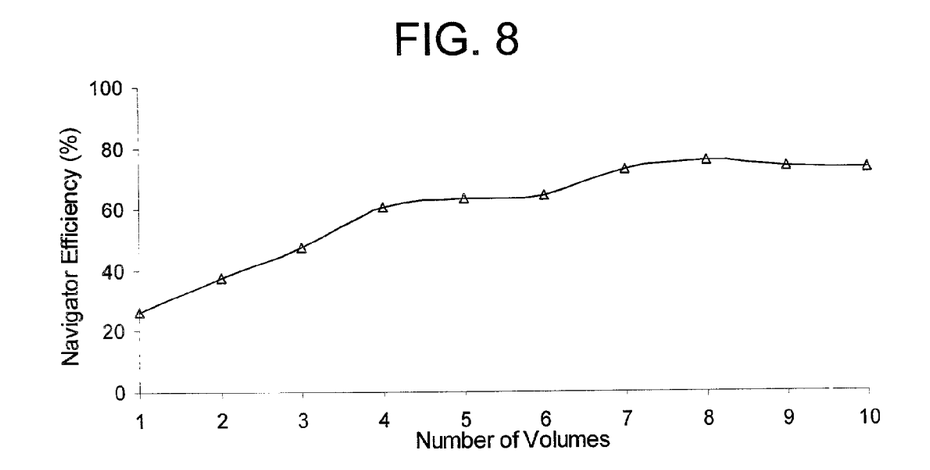
FIG. 8 is a graph illustrative of navigator efficiency compared to the number of volumes being simultaneously acquired.

Turning now to FIG. 8, the navigator efficiency on average versus the number of volumes being simultaneously acquired (with volumes sizes kept the same) is shown. The navigator efficiency for the simultaneous acquisition method increased with the number of volumes (2D sections) simultaneously acquired, with the rate of increase the greatest for the first 4 volumes. The scan efficiency reaches 60% with 4 volumes, 72% at 7 volumes, and 75% at 8 volumes and fluctuates around that level. This demonstrates that the navigator efficiency can be increased significantly by simultaneously acquiring multiple volumes at various positions, and that the average increase in efficiency improves as more volumes are acquired (~60% at 4 volumes). This simultaneous acquisition method increases the navigator efficiency while maintaining the same gating window or the same effectiveness of motion suppression, A method for utilizing data at multiple positions of a motion histogram has been described. The foregoing description of various embodiments of the invention has been presented for purposes of illustration and description. It is not intended to be exhaustive or to limit the invention to the precise embodiments disclosed. Numerous modifications or variations are possible in light of the above teachings. For example, different volumes acquired at different positions may be patched together using morphing algorithms to form a composite image of the subject by morphing image volumes that correspond to overlapping portions of the composite image. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A method of acquiring a plurality of image volumes of a subject in a magnetic resonance imaging device comprising the steps of:
   determining a motion histogram of the subject;
   assigning the plurality of image volumes to a plurality of position bins of the motion histogram, the plurality of position bins located at different positions of the motion histogram; and
   concurrently acquiring the plurality of image volumes.

2. The method of claim 1 further comprising the step of reassigning a remaining number of image volumes to the plurality of position bins after at least one of the plurality of image volumes is acquired.

3. The method of claim 1 further comprising the step of updating the motion histogram.

4. The method of claim 3 further comprising the step of reassigning the plurality of image volumes to the plurality of position bins after the motion histogram has been updated.

5. The method of claim 1 wherein each volume has a size and each position bin has a height, the method further comprising the step of assigning the size to be proportional to the height.

6. The method of claim 1 wherein the plurality of image volumes have equal sizes.

7. The method of claim 1 wherein multiple image volumes are assigned to one of the plurality of position bins.

8. The method of claim 1 wherein the step of assigning each image volume comprises the step of assigning each image volume to minimize a completion time of acquiring the plurality of image volumes.

9. The method of claim 1 wherein portions of an image volume acquired at different position bins are morphed to form the image volume.

10. A computer-readable medium having computer executable instructions for performing the steps of claim 1.

11. The computer-readable medium of claim 10 having further computer executable instructions for performing the step comprising reassigning the plurality of image volumes to the plurality of position bins after the motion histogram has been updated.

12. The computer readable medium of claim 10 wherein the step of assigning each image volume comprises the step of assigning each image volume such that a completion time of acquiring the plurality of image volume is minimized.

13. A method of scheduling the simultaneous acquisition of a plurality of image volumes of a subject using a magnetic resonance imaging device comprising the step of assigning the plurality of image volumes to a plurality of position bins of a motion histogram such that a scan time is minimal.

14. The method of claim 13 wherein the scan time of each image volume is calculated according to the equation scan time $= (N(v) - n(v,b))/h_b$ wherein $N(v)$ is the total number of data points in a volume $v$; $h_b$ is the frequency of the instantaneous histogram at bin $b$; $n(v,b)$ is the number of points acquired for volume $v$ at bin $b$.

15. The method of claim 13 further comprising the step of assigning at least one image volume of the plurality of image volumes to each position bin.

16. The method of claim 13 further comprising the step of updating the motion histogram.

17. The method of claim 16 further comprising the step of reassigning each remaining image volume to at least one of the position bins, each position bin having at least one image volume.

18. The method of claim 13 wherein the plurality of image volumes are assigned to the plurality of position bins subject to the constraint that upon completion each image volume has been acquired at one of the plurality of position bins.

19. The method of claim 13 further comprising the step of acquiring the image volumes.

20. The method of claim 19 wherein portions of an image volume acquired at different position bins are morphed to form the image volume.

21. A computer readable medium having computer executable instructions for performing the step of claim 13.

22. The computer readable medium of claim 21 having further computer executable instructions for performing the step of reassigning remaining image volumes to at least one of the position bins, each position bin having at least one of the remaining image volumes.

23. The computer readable medium of claim 21 wherein the step of assigning the plurality of image volumes to the plurality of position bins of the motion histogram includes assigning each image volume to at least one of the position bins such that each position bin is assigned at least one image volume.

24. The computer readable medium of claim 21 having further computer executable instructions for performing the step of updating the motion histogram.

25. The computer readable medium of claim 24 having further computer executable instructions for performing the step of reassigning remaining image volumes to the plurality of position bins.

26. A method of acquiring a plurality of image volumes of a subject in a magnetic resonance imaging device comprising the steps of:
   determining a motion histogram of the subject;
   assigning the plurality of image volumes to a plurality of position bins of the motion histogram, the plurality of position bins located at different positions of the motion histogram;
   concurrently acquiring the plurality of image volumes; and
   morphing the plurality of image volumes to form a composite image of the subject.

27. The method of claim 26 further comprising the steps of assigning the plurality of image volumes to the plurality of position bins such that a completion time of acquiring the plurality of images is minimized.

28. The method of claim 26 further comprising the step of assigning one of the plurality of image volumes to more than one position bin.

29. The method of claim 26 wherein each image volume corresponds to a portion of the composite image and wherein the step of morphing the plurality of image volumes to form the composite image of the subject comprises morphing image volumes that correspond to overlapping portions of the composite image.

* * * * *